(12) United States Patent
Sampath et al.

(10) Patent No.: US 10,966,833 B2
(45) Date of Patent: Apr. 6, 2021

(54) MODULATED ULTRA-SOUND COMPATIBLE ARTIFICIAL CRANIAL PROSTHESIS

(71) Applicants: Prakash Sampath, Providence, RI (US); Francesco Dimeco, Milan (IT)

(72) Inventors: Prakash Sampath, Providence, RI (US); Francesco Dimeco, Milan (IT)

(*) Notice: Subject to any disclaimer, the term of this patent is extended or adjusted under 35 U.S.C. 154(b) by 48 days.

(21) Appl. No.: 16/337,053

(22) PCT Filed: Sep. 27, 2017

(86) PCT No.: PCT/US2017/053847
§ 371 (c)(1),
(2) Date: Mar. 27, 2019

(87) PCT Pub. No.: WO2018/064239
PCT Pub. Date: Apr. 5, 2018

(65) Prior Publication Data
US 2020/0030099 A1  Jan. 30, 2020

Related U.S. Application Data

(60) Provisional application No. 62/400,607, filed on Sep. 27, 2016.

(51) Int. Cl.
*A61F 2/28* (2006.01)
*A61B 5/03* (2006.01)
(Continued)

(52) U.S. Cl.
CPC ............ *A61F 2/2875* (2013.01); *A61B 5/686* (2013.01); *A61B 8/0808* (2013.01);
(Continued)

(58) Field of Classification Search
CPC . A61F 2/2875; A61B 2090/103; A61B 5/031; A61B 17/688; A61N 1/0539
See application file for complete search history.

(56) References Cited

U.S. PATENT DOCUMENTS 5,397,361 A   3/1995  Clark
7,717,853 B2  5/2010  Nita
(Continued)

FOREIGN PATENT DOCUMENTS

WO  WO-2015032858 A1  3/2015
WO  WO-2016097867 A2  6/2016

OTHER PUBLICATIONS

PCT/US2017/053847, Modulated Ultra-Sound Compatible Artificial Cranial Prosthesis, Sep. 27, 2017.
(Continued)

*Primary Examiner* — David H Willse
*Assistant Examiner* — Javier G Blanco
(74) *Attorney, Agent, or Firm* — Alan F. Feeney; Feeney IP Law

(57) ABSTRACT

An intracranial prosthesis comprised of a flat body having an interior ultrasound-compatible window and means about the outer portion capable of engaging a plurality of diagnostic instruments and/or intracranial delivery systems so that a practicing medical professional can monitor certain parameters of a patient or deliver therapeutic agents to the patient while using an ultrasound-monitoring device to image the patient's brain. The prosthesis is designed to allow for the continuous, uninterrupted, simultaneous monitoring of a number of parameters of a patient's brain at the patient's bedside.

6 Claims, 12 Drawing Sheets

(51) Int. Cl.
| | |
|---|---|
| *A61B 5/00* | (2006.01) |
| *A61B 8/08* | (2006.01) |
| *A61B 8/00* | (2006.01) |
| *A61B 5/01* | (2006.01) |
| *A61B 5/026* | (2006.01) |
| *A61B 5/055* | (2006.01) |
| *A61B 5/1455* | (2006.01) |
| *A61B 10/02* | (2006.01) |
| *A61B 90/10* | (2016.01) |
| *A61B 17/68* | (2006.01) |
| *A61N 1/05* | (2006.01) |

(52) U.S. Cl.
CPC .......... *A61B 8/4272* (2013.01); *A61B 8/4416* (2013.01); *A61B 5/01* (2013.01); *A61B 5/026* (2013.01); *A61B 5/031* (2013.01); *A61B 5/055* (2013.01); *A61B 5/14553* (2013.01); *A61B 5/4839* (2013.01); *A61B 10/02* (2013.01); *A61B 17/688* (2013.01); *A61B 2090/103* (2016.02); *A61B 2560/0443* (2013.01); *A61F 2220/0008* (2013.01); *A61F 2250/0093* (2013.01); *A61N 1/0539* (2013.01)

(56) References Cited

U.S. PATENT DOCUMENTS

| | | | |
|---|---|---|---|
| 8,298,292 | B2 | 10/2012 | Swords et al. |
| 9,044,195 | B2 | 6/2015 | Manwaring et al. |
| 9,592,124 | B2 | 3/2017 | Joganic |
| 2004/0243145 | A1 | 12/2004 | Bobo, Sr. et al. |
| 2006/0195190 | A1 | 8/2006 | Lechmann et al. |
| 2006/0224242 | A1 | 10/2006 | Swords et al. |
| 2007/0129652 | A1 | 6/2007 | Nita |
| 2008/0319376 | A1* | 12/2008 | Wilcox ............... A61M 25/003 604/22 |
| 2011/0009739 | A1 | 1/2011 | Phillips et al. |
| 2014/0074202 | A1 | 3/2014 | Bedenbaugh |
| 2014/0330123 | A1 | 11/2014 | Manwaring et al. |
| 2016/0193048 | A1 | 7/2016 | Prada |

OTHER PUBLICATIONS

Chatterjee, Sandip, and L. Harischandra. "Cerebrospinal fluid shunts—How they work: The basics." Neurology India 66.1 (2018): 24.
Longeviti Neuro Solutions, Introducing the Invisishunt (Brochure), longeviti.com, 2017.
Longeviti Neuro Solutions, ClearFit (Brochure), longeviti.com, 2017.
CIPO, Examination Report, dated Apr. 16, 2020, re Canadian Patent Application No. 3038668.
ISA/US, International Preliminary Report on Patentability (Ch.1), dated Apr. 11, 2019, re PCT International Patent Application No. PCT/US2017/053847.
EPO, Extended European Search Report, dated Apr. 21, 2020, re European Patent Application No. 17857377.0.
ISA/US, International Search Report, dated Nov. 30, 2017, re PCT International Patent Application No. PCT/US2017/053847.
ISA/US, Written Opinion, dated Nov. 30, 2017, re PCT International Patent Application No. PCT/US2017/053847.

* cited by examiner

MODULATED ULTRA-SOUND COMPATIBLE ARTIFICIAL CRANIAL PROSTHESIS

CROSS-REFERENCE TO RELATED APPLICATIONS

This application is a continuation under 35 U.S.C. § 371 of International Application No. PCT/US2017/053847 filed on Sep. 27, 2017, which claims priority to U.S. Provisional Patent Application Ser. No. 62/400,607 filed Sep. 27, 2016, which is hereby incorporated by reference herein in its entirety.

BACKGROUND OF THE INVENTION

The present invention relates to an ultrasound-compatible cranial prosthesis, with modular capabilities, used as a "window" into the cranial vault.

Surgical efforts to repair cranial defects commonly occur. For example, various types of surgical procedures on the human brain require removal of a portion of the skull. By way of example only, those include surgeries that remove brain tumors, reduce brain swelling, repair cerebral aneurysms, evacuate hematomas, remove shrapnel and bullets secondary to trauma, drain abscesses and other intracranial infections, address congenital defects of the brain, as well as surgeries required to reconstruct damaged portions of the skull. The use of intra-operative imaging methods, i.e. of techniques to obtain images that provide diagnostic information, now plays an essential role in the carrying out of neurosurgical procedures, making it possible to optimally plan a procedure and enabling the anatomical and functional definition of the region of the brain in question. Furthermore, imaging methods can help the orientation of the neurosurgeon during a procedure. For example, the intra-operative use of ultrasound in neurosurgery, by placing the ultrasound probe directly on the brain surface, enables an excellent definition of cerebral anatomy and can help distinguish normal brain from pathological lesions.

The use of brain imaging continues in the immediate post-operative phase, in order to evaluate the brain anatomy and potentially the efficacy of peri-operative treatments. These treatments could include corticosteroids, mannitol, antibiotics, anticoagulants, radiation or chemotherapy. Such therapies, however, can have marked side effects and it is often difficult to determine their efficacy with current imaging techniques (e.g. Computed Tomography or Magnetic Resonance Imaging) in real time. Furthermore, some patients may not respond to a certain procedures and/or adjuvant therapies in a timely manner necessitating the need to continually monitor and identify such cases and apply different treatments. Early identification of these patients, in addition to improving their treatment, would result in a considerable economic saving and potentially superior patient outcomes.

Although ultrasound is a widely-used tool in the field of general diagnostic radiology, it is limited to very few areas in cerebral diagnostics. In fact, in the post-operative (follow-up) period, the highly hyperechogenic nature of the calvarium prevents ultrasound from penetrating into the cranial cavity, with the exception of the ocular and temporal acoustic fenestra. Repositioning or replacing the bone flap, removed following the neurosurgical procedure, in fact constitutes a barrier to ultrasound penetration and does not allow follow-up imaging of the patient using ultrasound.

The same occurs when the craniotomy site is reconstructed using a prosthesis according to prior art solutions. For instance, US-2006/224242 (University of South Florida) discloses an implant for reconstruction of craniofacial defects which uses a composite structure comprised of a surgical grade metal provided in a planar or curved sheet form that is encased within a malleable biocompatible material, such as a polyolefin, in high density polyethylene. WO 2015/032858 (Prada) discloses an ultrasound compatible, artificial cranial operculum requiring replacement of the bone flap.

Although occasionally available, the ultrasound methods used to get past the calvarium/skull and/or prosthesis still do not enable an accurate and definite evaluation of the intracranial contents including the brain parenchyma and ventricles.

BRIEF SUMMARY OF THE INVENTION

The aim of the present invention is to enable an effective use of ultrasound in cerebral diagnostics and to further use the claimed device as a platform onto which other diagnostic, delivery, and/or therapeutic devices may be launched, so as to make it possible to perform complete, post-operative imaging of the intracranial contents in real time. In addition, the device will have modulations that can monitor the progress of an intracranial pathology, as well as utilizing the device to administer and deliver therapies when necessary. Finally the device would facilitate therapeutic ultrasound application including blood brain barrier disruption, blood clot liquefication, and high intensity focused ultrasound treatment for brain lesioning.

In accordance with the invention, such aim is achieved by way of a cranial prosthesis to replace a bone window or incorporated into a bone flap removed from a cranium during a neurosurgical procedure which comprises a craniotomy or craniectomy; said cranial prosthesis being characterized in that it is made of a material that is rigid, biocompatible, sterilizable, and compatible with ultrasound and with nuclear magnetic resonance and further capable of accommodating various diagnostic tools, delivery vehicles, and instruments into said cranial prosthesis which are used for modular capacity.

The outer rim of the invention will house the modular components of said device and has the capacity to rotate such that a given modulation can reside in the optimal position as desired by the surgeon.

The characteristics of the present invention will be made clear by the following detailed description of an embodiment thereof, which is illustrated by way of non-limiting example in the accompanying drawings.

BRIEF DESCRIPTION OF THE DRAWINGS

The present disclosure may be better understood with reference to the following figures. Matching reference numerals designate correspondence parts throughout the figures which are not necessarily drawn to scale.

FIGS. 5A-5C illustrate the rotational capability of the prosthesis and its ability to re-locate the various modulated devices without removing the device from the patient.

It should be appreciated that the fastening holes, access ports and modulated devices are not drawn to scale and that varying sizes of each are encompassed in the scope of the claimed cranial prosthesis. It should also be appreciated that the modulated devices depicted in FIGS. 4A-4D and 5A-5D are merely provided for illustrative purposes only and that the instant cranial prosthesis is not limiting to use of these devices only. The modulated devices may be inserted further into the patient's brain than as depicted in the aforementioned figures. In addition, the modulated devices may be inserted anywhere in the intracranial vault as depicted in the aforementioned figures.

DETAILED DESCRIPTION OF THE INVENTION

Figure 1A:
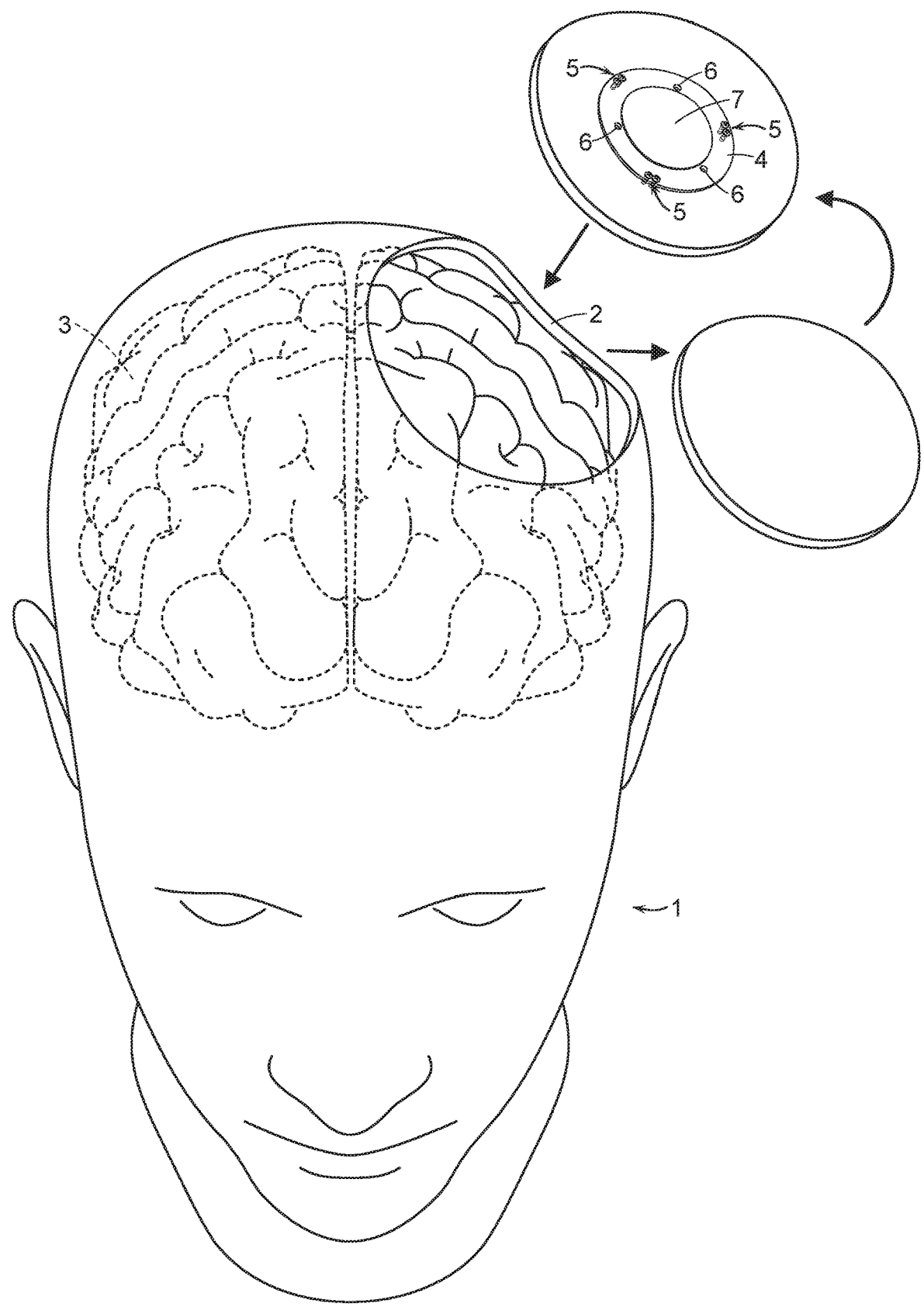
FIG. 1A illustrates the incorporation of the claimed prosthetic device into the removed bone flap which is then reattached to the patient.
Figure 1B:
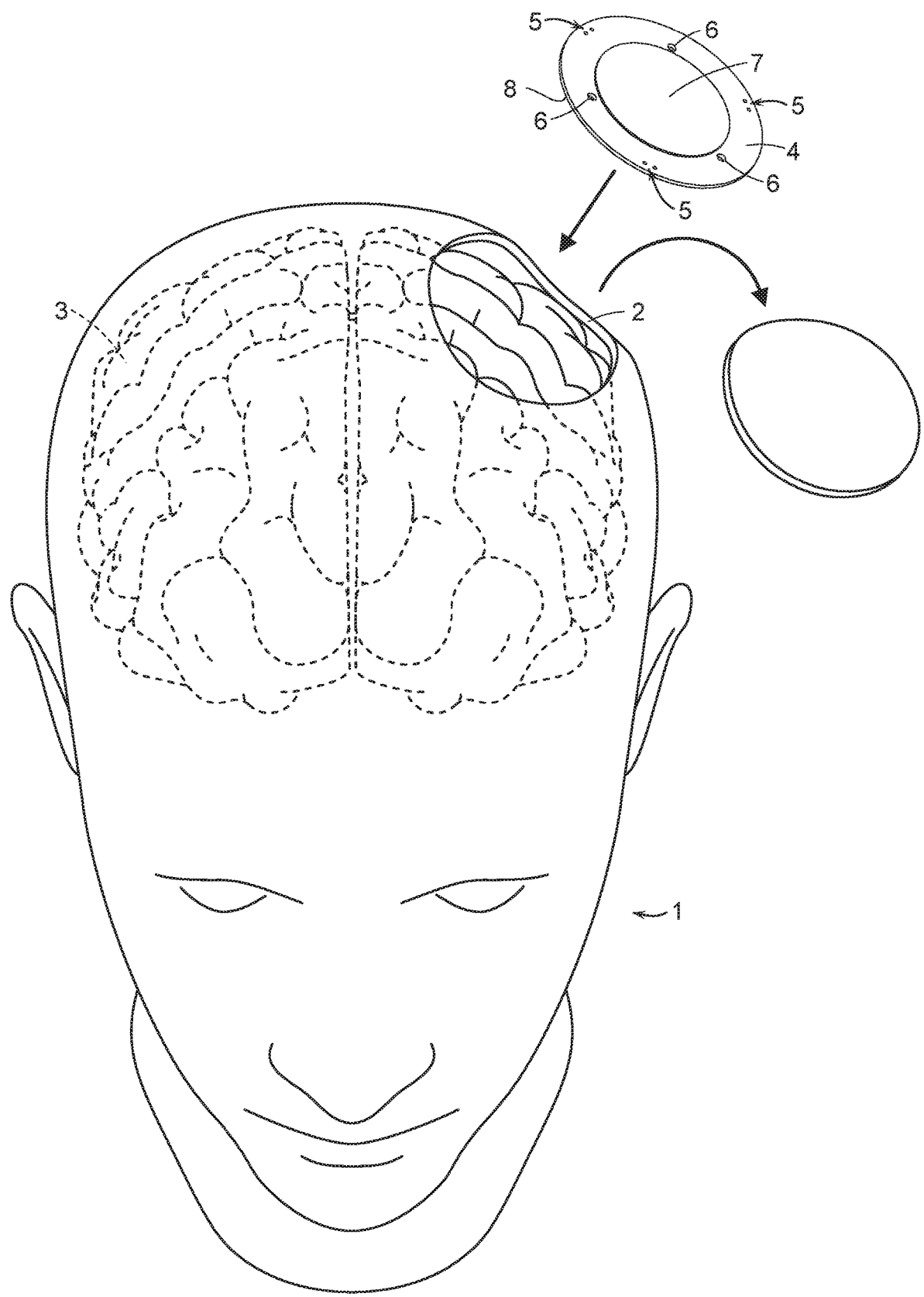
FIG. 1B illustrates the replacement of the intracranial flap with the claimed prosthetic device.
Figure 1C:
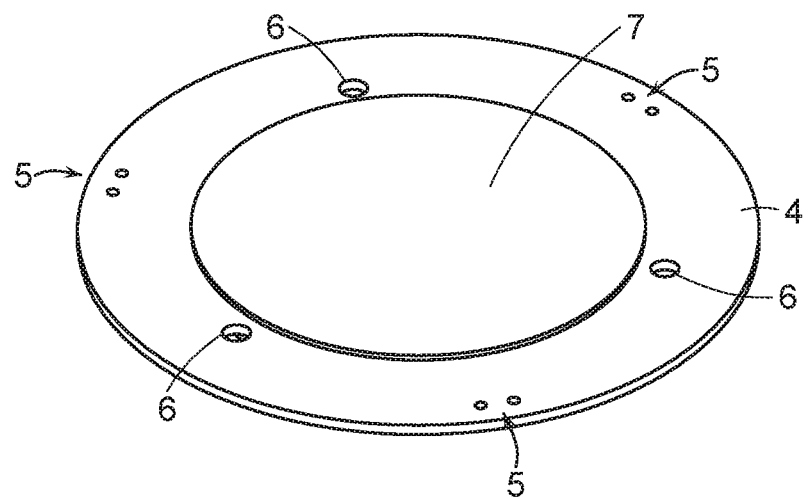
FIG. 1C is a partial side view of the instant prosthesis showing an embodiment having three inner access ports and three pairs of bores for cranial fastening.
Figure 1D:
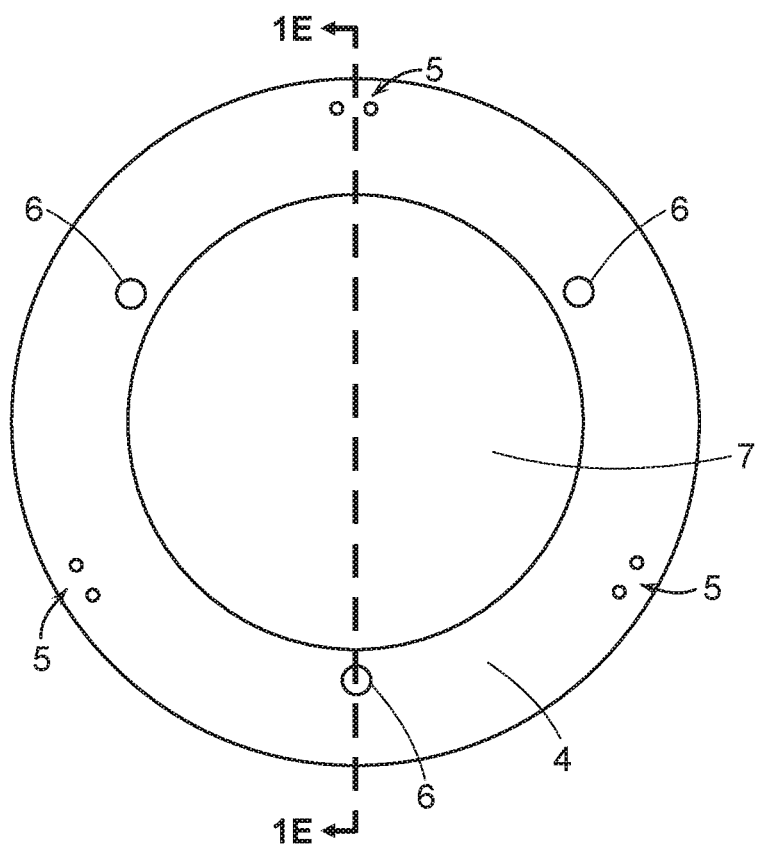
FIG. 1D is a view from the top of the prosthesis illustrating the arrangement of the inner, ultrasound compatible disc and the outer modulation ring. The dotted line 1E indicates what part of the prosthetic device is depicted in the cross-sectional view depicted in FIG. 1E.
Figure 1E:
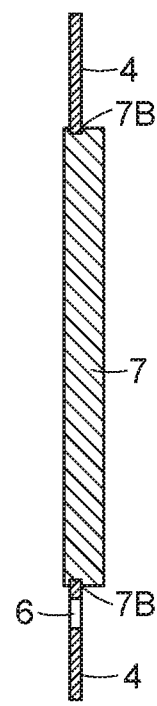
FIG. 1E is a cross-sectional view of the prosthesis illustrating the interaction between the inner, radio-lucent disc and the outer modulation ring.
Figure 2B:
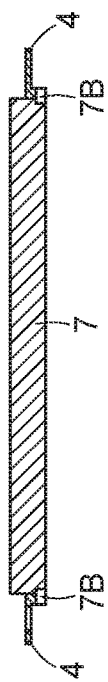
FIG. 2B is a cross-sectional, side view of the fixed cranial prosthesis wherein the inner, radio-lucent disc is secured to the outer modulation ring with a press-fit. There is a slight inner protruding ridge or groove 7B from the outer ring into which the press fit radio-lucent disc is secured to prevent it from becoming depressed below the inner cortical bone mantle and compressing the dura.
Figure 2C:
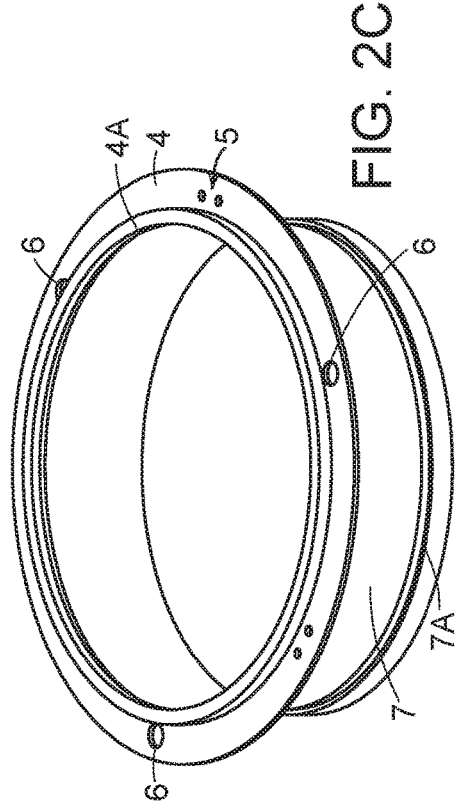
FIG. 2C is an exploded view from the perspective of the bottom of the cranial prosthesis illustrating the groove formed into the outer edge of the inner, ultra-sound compatible disc and the outer modulation ring having an internal, circular flange which, when press-fitted into the aforementioned groove, secures the inner, radio-lucent disc to the outer modulation disc.
Figure 2A:
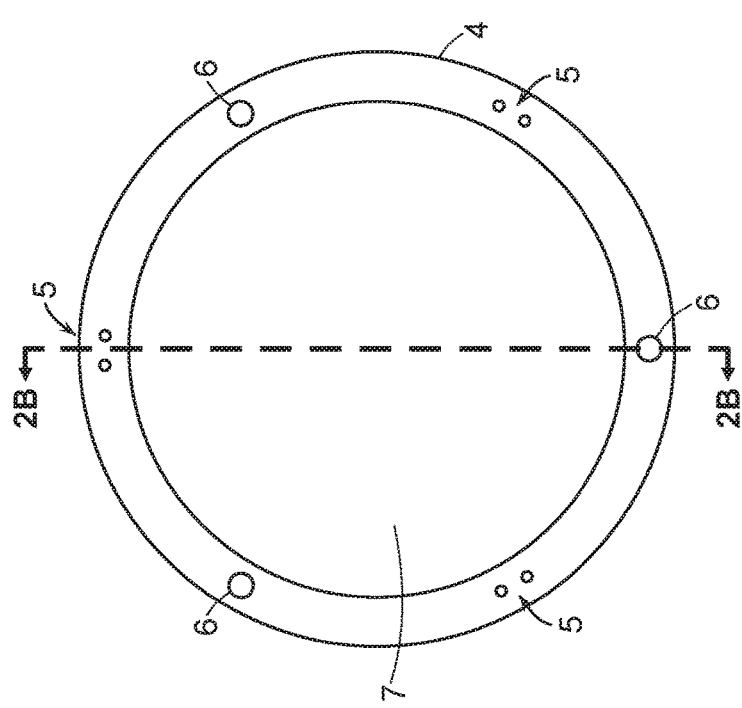
FIG. 2A is a diagram of the fixed cranial prosthesis of the second embodiment wherein the inner, radio-lucent disc is secured into the modulation ring with a press fit. The dotted line 2B indicates what part of the prosthetic device is depicted in the cross-sectional view depicted in FIG. 2B.
Figure 3:
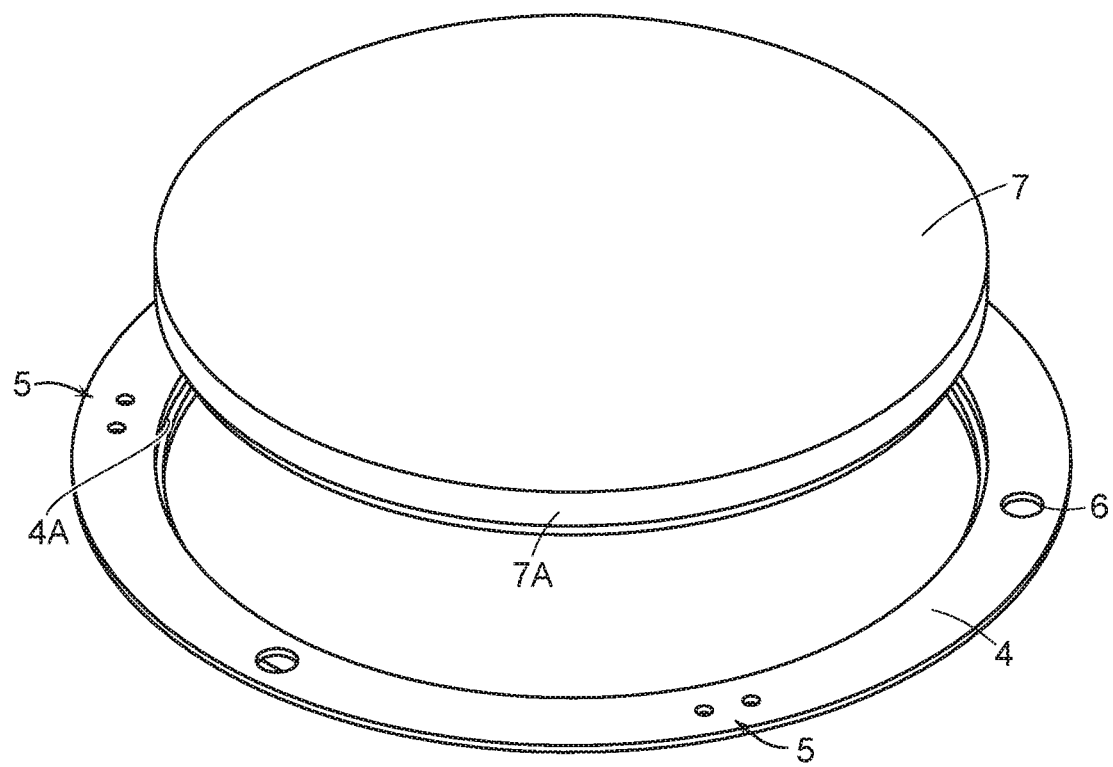
FIG. 3 is an exploded view of the claimed cranial prosthesis depicting the inner, ultrasound compatible disc prior to installation by press-fit into outer modulation ring.
Figure 4A:
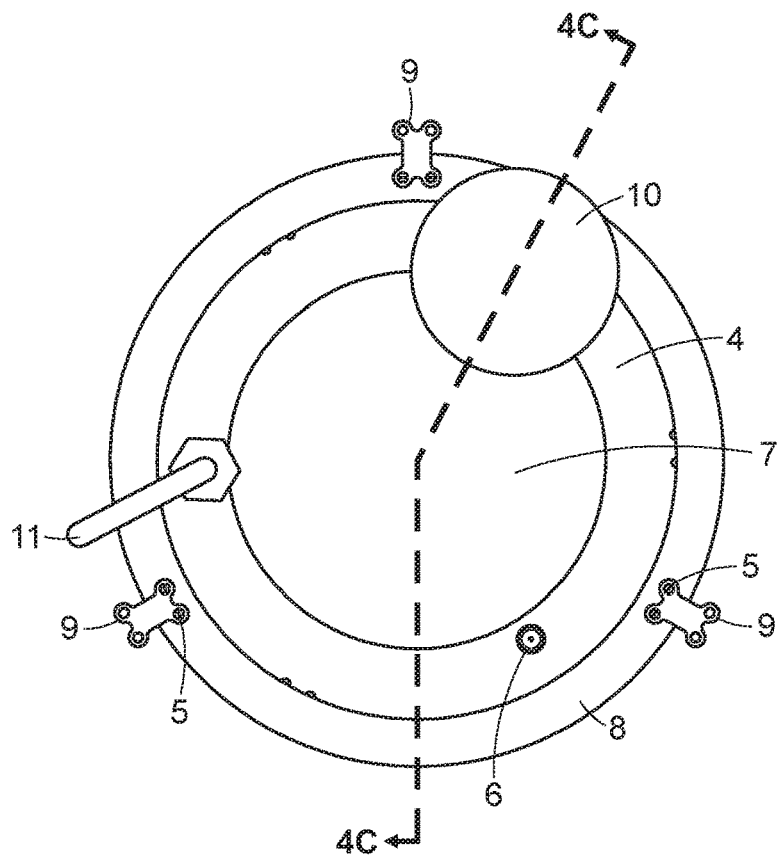
FIG. 4A is a top view of a fully modulated embodiment of the rotation cranial prosthesis.
Figure 4B:
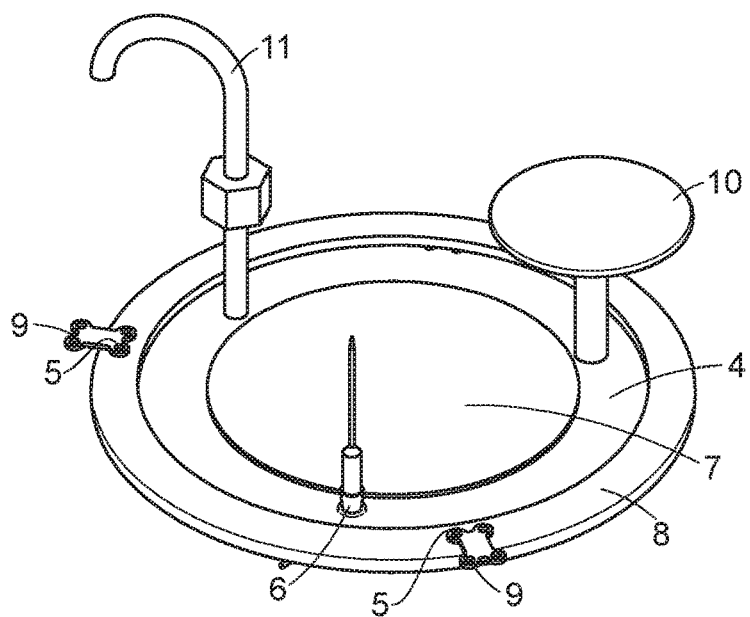
FIG. 4B is a side view of FIG. 4A illustrating an embodiment of the rotational cranial prosthesis wherein an ICP monitor, a specialized delivery vehicle and a cranial access device have all been incorporated into the outer modulation ring.
Figure 4C:
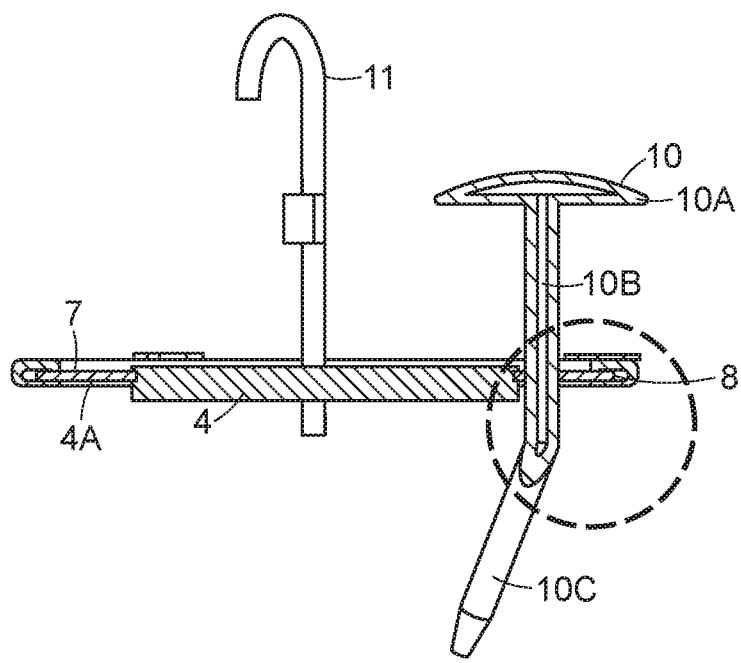
FIG. 4C is a cross-sectional side view of part of FIG. 4B showing the rotational cranial prosthesis with an ICP monitor installed therein and the catheter of a cranial access device having been inserted into the brain of the patient. The section of this figure contained in the dotted circle is the cross section view of FIG. 4D.
Figure 4D:
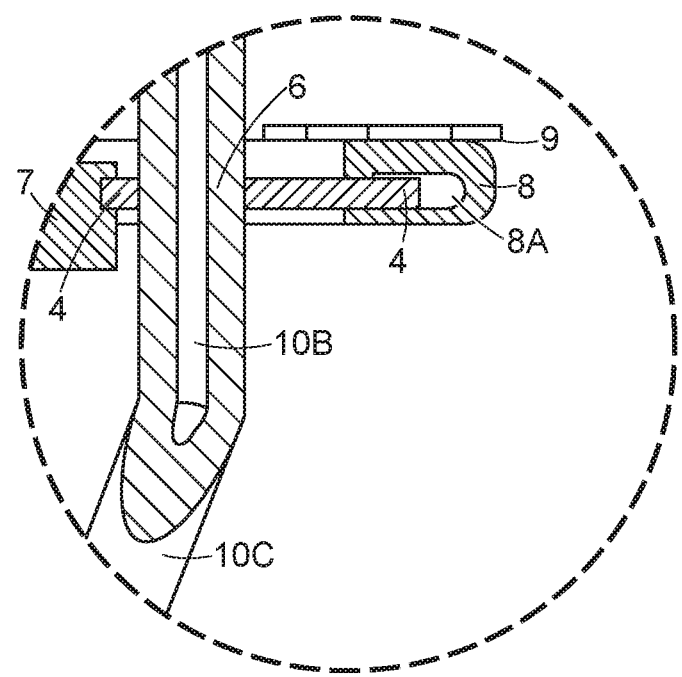
FIG. 4D is an enlarged view of the cross-sectional view of FIG. 4C illustrating the means in which the catheter of the cranial access device is maintained by the access port of the outer modulation ring.
Figure 5B:
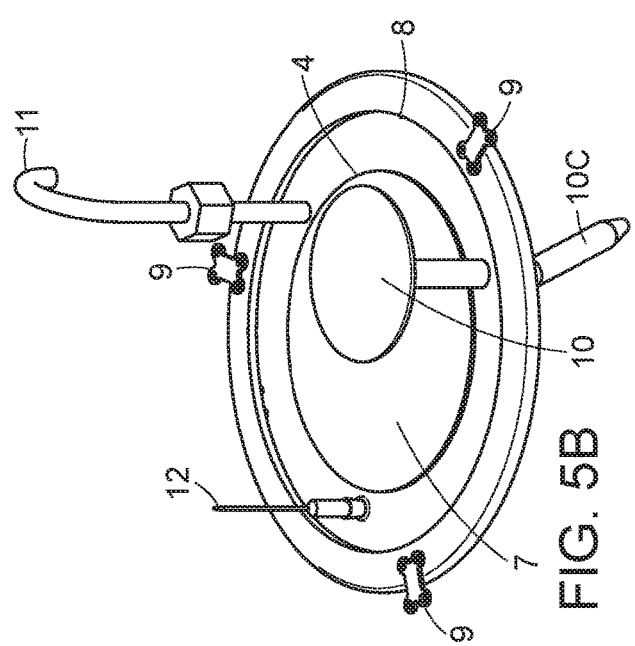
FIGS. 5A-5C depict various views of the rotational cranial prosthesis after an ICP monitor, an enhanced delivery vehicle and a cranial access device have all been incorporated into the outer modulation ring. Taken together.
Figure 5D:
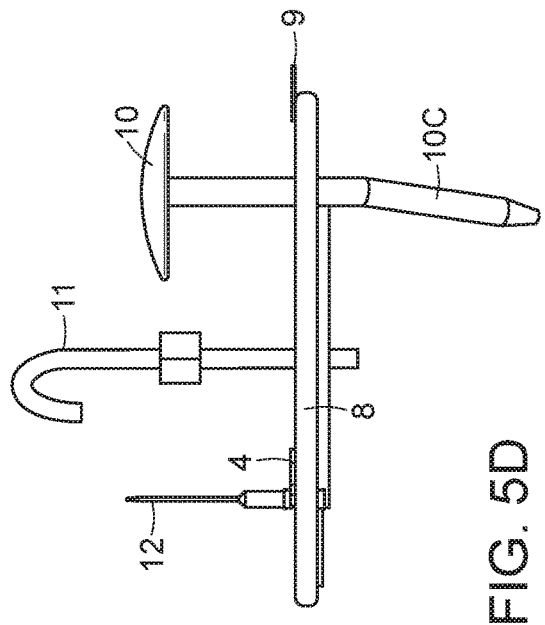
FIG. 5D is a side view of the rotational cranial prosthesis after an ICP monitor, an enhanced delivery vehicle and a cranial access device have all been incorporated into the outer modulation ring.
Figure 5A:
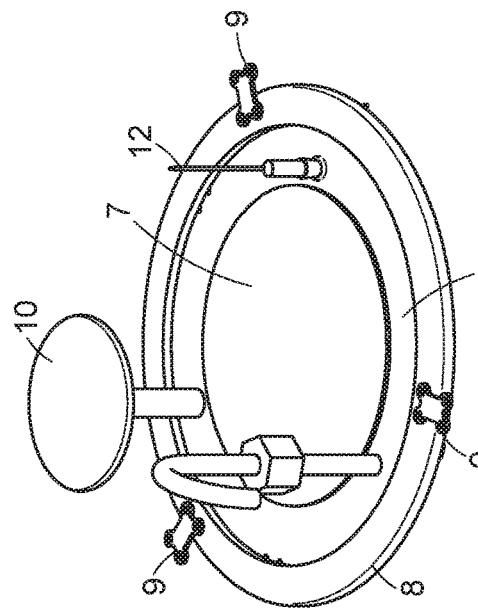
Figure 5C:
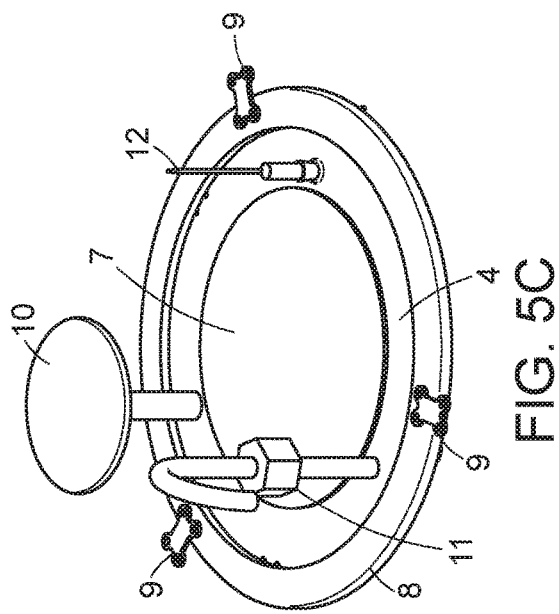
Figure 6A:
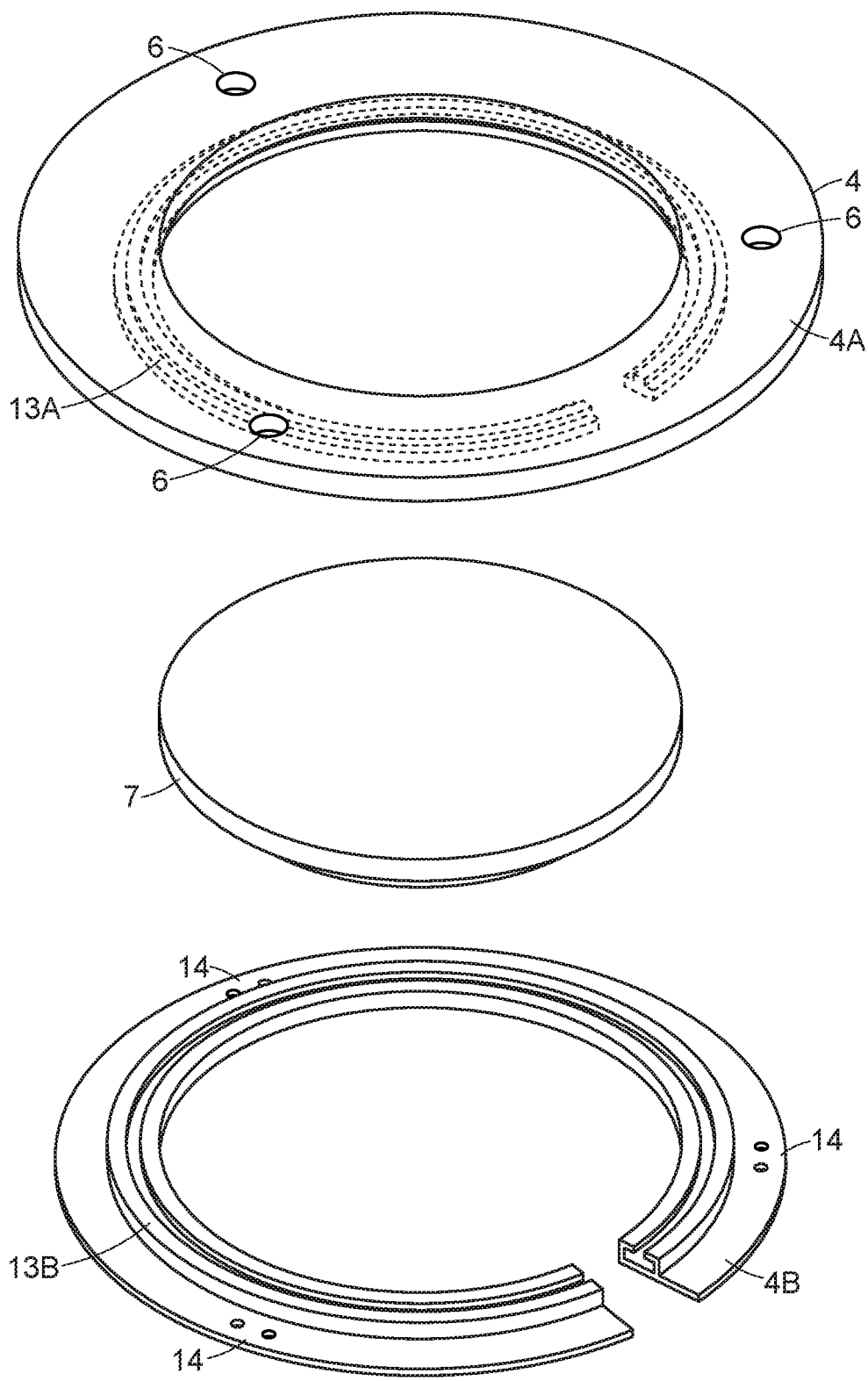
FIG. 6A is an exploded view of the ring structure of the fourth embodiment (the inner, radio-lucent disc is not shown) having a modulation ring comprising an upper and lower ring.
Figure 6B:
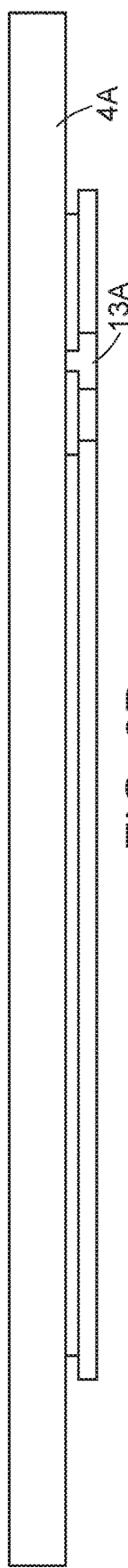
FIG. 6B is a side view of the upper ring with the nail and head configuration.
Figure 6C:
FIG. 6C is a side view of the lower ring with the running track.
Figure 6D:
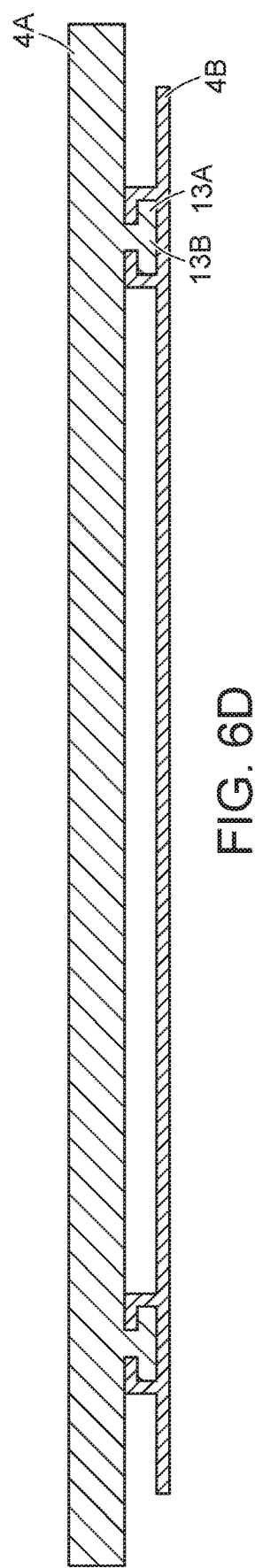
FIG. 6D is a cross-sectional view of the nail and head configuration of the upper ring (or the lower ring) as it interacts with the running track of the lower ring (or the upper ring).
Figure 6E:
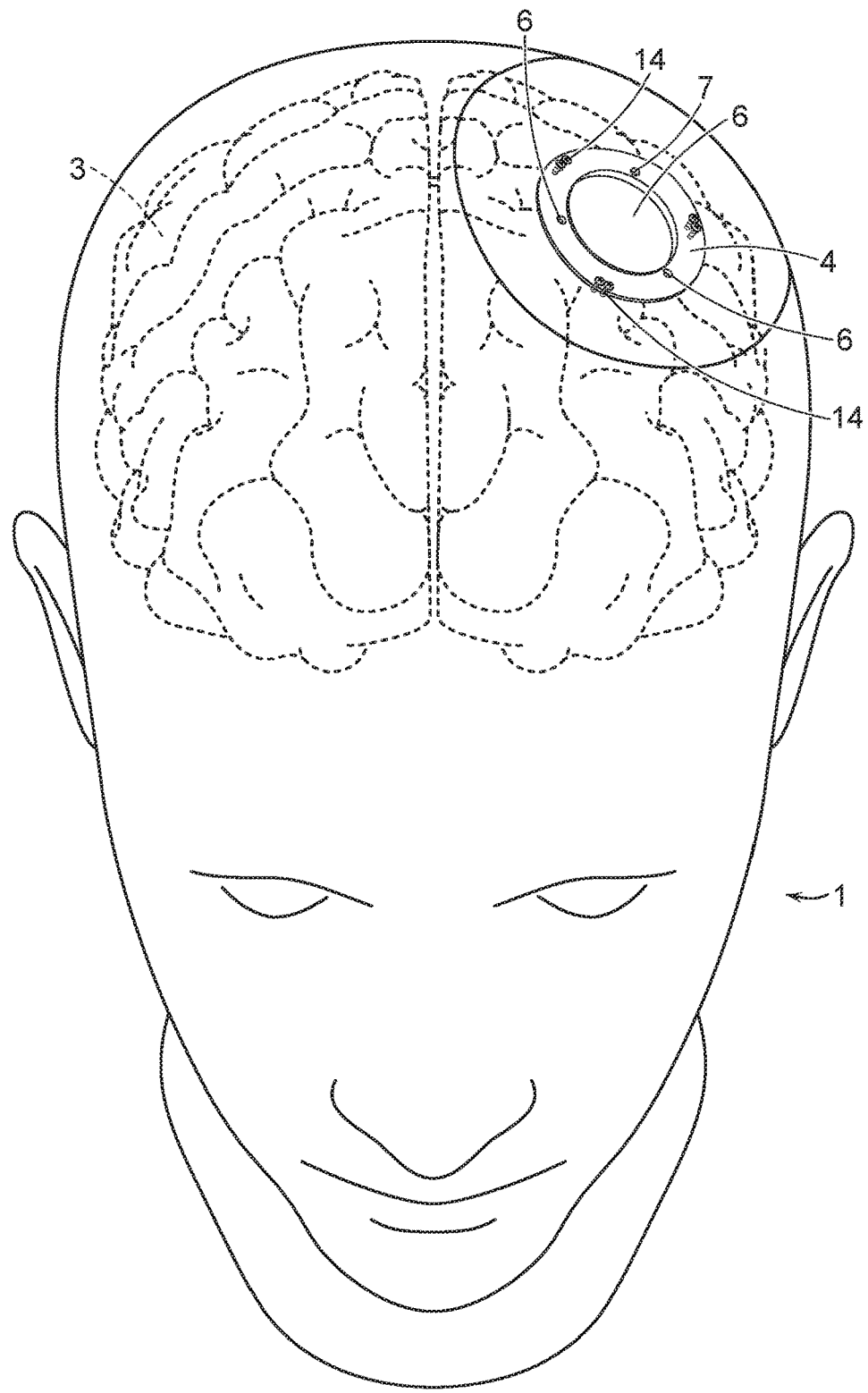
FIG. 6E is a top view of the intracranial prosthesis after it has been secured to the cranium of the patient. In this depiction titanium plates secure the bottom ring of the lower ring to the cranium of the patient.
Figure 6F:
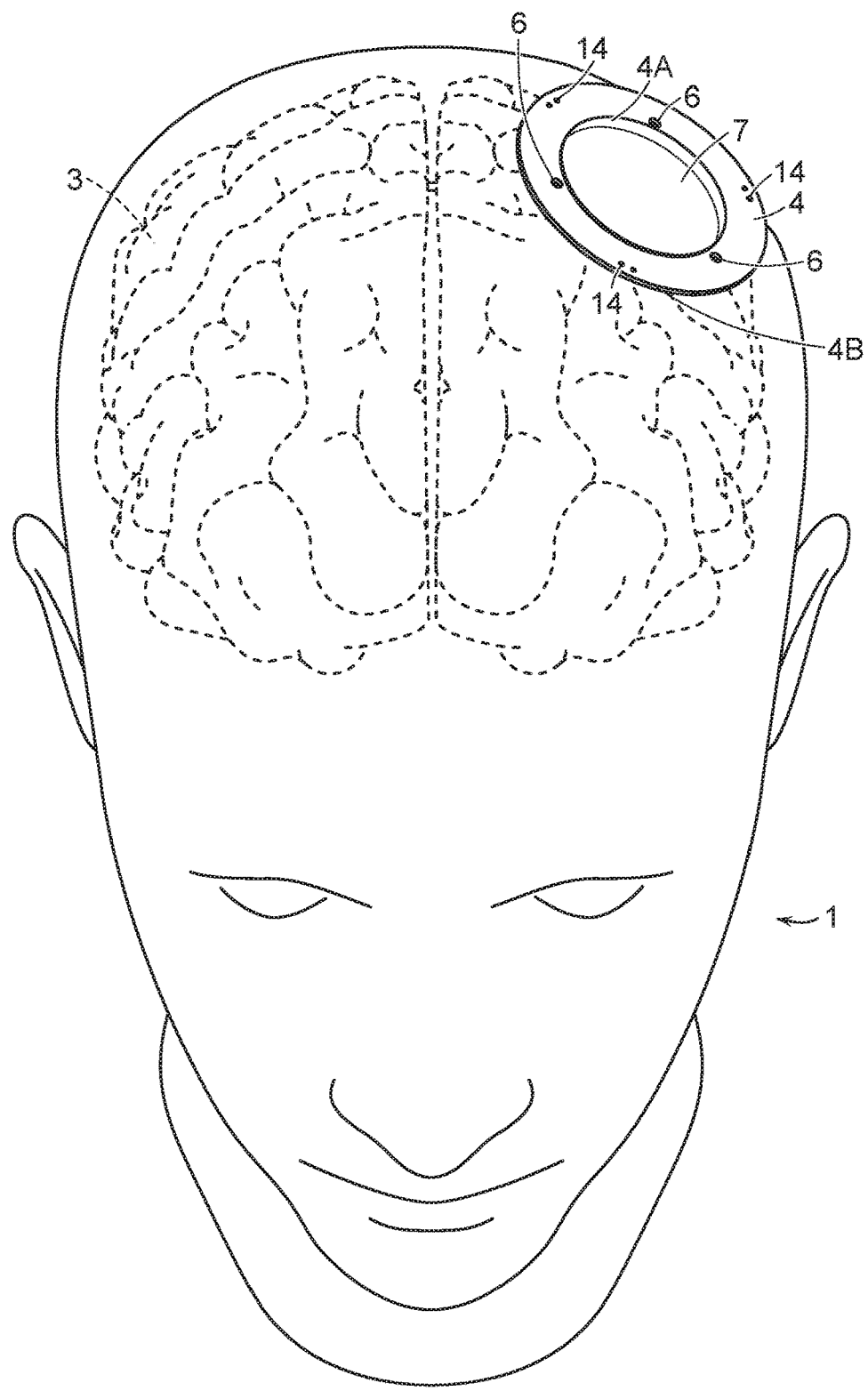
FIG. 6F is a top view of the intracranial prosthesis after it replaces the section of the cranium of the patient removed prior to surgery on the patient's brain. In this depiction titanium plates secure the bottom ring of the lower ring to the cranium of the patient.

The cranial prosthesis FIGS. 1C-1E according to the present invention is comprised of an inner, ultra-sound compatible disc 7 surrounded by an outer, rigid ring. The outer rigid ring 4 is configured to accept, i.e. "modulate", a variety of diagnostic tools 10-12 and devices to monitor various conditions of the brain whilst the treating surgeon uses ultrasound technology to image the brain from the inner disc 7. In a second embodiment FIGS. 2A-2C and FIG. 3, the inner disc 7 is formed with a circumferential groove 7A to accept a circular flange 4A of the inner circumference of the outer ring 4 securing the inner disc 7 to the outer ring 4 by a "press fit." In yet another embodiment FIGS. 4A-4D and FIGS. 5A-5D, the device further comprises an outer casing 8 which allows for the rotation of the outer ring 4. The rotation of the outer ring 4 allows for the positioning or re-positioning (in the event of re-operation) of the access ports 6 found in said ring 4 at the desired site in need of treatment aided using ultrasound imaging through the ultrasound compatible inner disc 7. In yet another embodiment FIGS. 6A-6E, the outer modulation ring 4 is comprised of two rings 4A and 4B wherein the top ring 4A has a nail and head configuration 13A formed into its bottom side and the lower ring 4B has an opposing running track configuration 13B on its top side so that when said nail and head configuration 13A engages FIG. 6D said running track configuration 13B, the top ring 4A is rotatably secured to the device by the bottom ring 4B.

The cranial prosthesis is made of rigid material which will be used to substitute a bone flap FIG. 1B or be incorporated into a bone flap FIG. 1A that has been removed to perform a craniotomy to access the intracranial cavity, in order to perform a procedure on the brain 3 or its surroundings of the patient 1. So that the artificial cranial prosthesis will be inert with no damaging effects for the patient 1, it is necessary that it be made of a material that is biocompatible and which is also sterilizable before application.

The cranial prosthesis may be incorporated into the existing bone flap or in lieu of the bone flap after a craniotomy. The prosthesis may have holes 5 that are adapted to secure it to the surrounding skull 2 by way of suture thread, braces, screws, plates 9, bone anchors, sutures, wires or other U.S. Food and Drug Administration (FDA)-approved hardware capable of securing the prosthesis to the patient. In the preferred embodiment, a brace 9 having two sets of screw holes allows the user to secure the device to the remaining cranium of the patient with standard titanium mini-plates.

The claimed cranial prosthesis, which is intended to substitute the removed bone cranial operculum or be incorporated into the bone flap, is made of a material that is compatible with ultrasound, i.e. of a material that offers no resistance to the passage of ultrasound such that ultrasound technology can be utilized by the bedside with real time imaging. Furthermore, the cranial prosthesis is also (nuclear magnetic resonance) NMR-compatible to allow for MRI imaging.

The cranial prosthesis of the instant application can be either pre-fabricated in a number of sizes, i.e. small, medium and large, or may be custom-made using an additive manufacturing process ("3D printing"), constructed using a molding, vacuum forming, die pressing, machining or thermal forming process, or any other known or yet to be discovered manufacturing process. The ultrasound inner disc of the cranial prosthesis of the instant application may also be made in situ using a plastic resinous material that is moldable for a brief period and then sets, for example Cranioplastic® (L. D. Caulk Co., Milford, Del.) or an alginate (COE Laboratories, Inc., Chicago, Ill.) and an adjustable mold. It is important that whatever material used be FDA (or a similar regulating body from a word-wide equivalent of the FDA) compliant and, as mentioned previously, be biocompatible and able to be sterilized without damage to the prosthesis.

In the first embodiment of the instant invention FIGS. 1C-1E, the cranial prosthesis is comprised of an inner radio-lucent disc 7 having a planar or curved body unitarily formed from a single piece of material that can allow the use of ultra-sound diagnostic instruments. The radio-lucent section 7 should be constructed so as to prevent the creation of artifacts and/or causing visual impairment. Surrounding the radio-lucent section is an outer modulation ring 4 having a plurality of access ports 6 capable of introducing one or more diagnostic instruments or delivery vehicles 10-12, i.e. "a module", into the brain of the patient. Said diagnostic instruments 10-12 may be integrated into said outer modulation ring 4 of the cranial prosthesis, either permanently or on a need basis, so that said module is operative while engaged with the cranial prosthesis. The instant device is designed in such a way as to allow for the ultrasound imaging of the brain of the patient while the modulated diagnostic instruments are functioning. The preferred material used to construct the outer modulation ring is silicone, polyoxymethylene (POM), polytetrafluoroethylene (PTFE), polyethylene or a biocompatible, FDA approved metal, such as stainless steel, but more particularly titanium. It should be appreciated that both the inner radio-lucent disc 7 and the outer modulation ring 4 may be made from the same material.

In the second embodiment of the instant invention FIGS. 2A-2C and FIG. 3, a circumferential groove 7A or indentation is formed into the side of the inner, ultrasound compatible disc 7. The outer modulation ring 4 is formed with an inner, circumferential flange 4A wherein said inner disc is secured to the outer modulation ring by a press-fit FIG. 3. In particular, the inner, circumferential flange 4A engages the circumferential groove 7A of the inner, ultrasound compatible disc 7. In this embodiment, the practitioner is able to position the outer ring 4 by rotation so that the access ports 6 are in a desired position. Using fastening means (not shown), the practitioner can secure the outer ring 4 to the cranium 2 of the patient 1 and thereafter secure the inner, ultrasound-compatible inner disc 7 to the outer ring 4. In the alternative embodiment depicted in FIG. 2B, the inner, ultrasound compatible disc 7 may be formed with outwardly extending flange 7B capable of engaging an inward groove (not shown) of the outer modulation ring 4 by a press fit securing the disc 7 to the outer ring 4.

In the third embodiment of the claimed invention FIGS. 4A-4D and FIGS. 5A-5D, the inner, ultrasound compatible disc 7 is permanently secured to the outer, modulation ring 4. The outer, modulation ring 4 with the inner ultrasound compatible disc 7, fit within an outer casing 8 having an inner space 8A which receives the outer modulation ring 4/inner disc 7. The outer casing 8 includes means 9 in which to secure the device to the remaining cranium 2 of the patient 1. Once implanted onto the brain 3 of the patient 1, the outer casing 8 secures the modulation ring 4/inner disc 7 to the patient 1. The outer modulation ring 7 is able to freely rotate within the space 8A of the outer casing 8 providing the practitioner with the ability to position an access port (not shown) over the desired location aided by the ultrasound imaging. The outer casing 8 has means of securing 9 the device to the cranium 2 of the patient 1 using suture thread, braces, screws, plates 9, bone anchors, sutures, wires or other FDA-approved hardware. After installation, the surgeon can loosen the fastening devices 9 to rotate the modular ring 4 so as to monitor and/or administer therapeutic drugs to different areas of the patient's brain without having to remove the device. This would be an especially important in the event of re-operation for intracranial pathology. FIGS. 5A-5D depict a fully-modulated (for this version) prosthesis modulated with a cranial access device 10, an ICP monitor 11, and a convection enhanced delivery vehicle 12.

In the fourth embodiment FIGS. 6A-6F, the claimed cranial prosthesis comprises an inner radio-lucent disc 7 having a generally planar or curved body unitarily formed from a single piece of material that is capable of allowing the use of ultrasound diagnostic instruments and intracranial delivery systems as discussed above. Surrounding the inner disc 7 is an outer ring structure 4 comprising an upper ring 4A and a lower ring 4B. A circular running track 13B is formed into the lower ring 4B. The upper ring 4A is formed with a nail and head 13A configuration that fits within the running track 13B of the lower ring 4B. Once secured in the running track 13B of the lower ring 4B, the nail and head configuration 13A slides along said running track 13B keeping the upper ring 4A in a fixed position as the upper ring 4A is rotated by the practitioner. The lower ring 4B, which maintains the positioning of upper ring 4A when in use, has means in which to secure the ring assembly 4 to the cranium 2 of the patient 1. It should be appreciated that the upper ring 4A may be formed with the running track 13B and the lower ring 4B with the nail and head configuration 13A. The inner disc 7 is preferably affixed to the lower ring 4B and the upper ring 4A rotates about it when in use. The inner disc 7 may include means in which to allow the upper ring 4A to rotate without encumbrance, such as a groove formed into its edge 7A or a circumferential, frictionless ribbon (not shown) made from an FDA-approved material. It is preferred that the portion of the lower ring 4B that surrounds the running track 13B or nail and head 13A configuration should be flat whereas the upper ring 4A may have an upward arch. The upper ring 4A may also contain a locking means (not shown) to hold it in place once the practitioner has determined the desired location for the access ports 6. The lower ring 4B must have a width that is narrower than the width of the upper ring 4A so that the access ports 6 found in the upper ring 4A are not blocked by the lower ring 4B so as to provide full access to the brain 3 to insert the desired diagnostic devices 11 and/or intracranial delivery vehicles 12 and/or intracranial access means 10.

The outer modulation ring 4 is comprised of an FDA approved material such as silicone, polyoxymethylene (POM), polytetrafluoroethylene (PTFE), polyethylene, or a biocompatible, FDA approved metal, such as titanium, titanium alloy or cobalt chrome. In the preferred embodiment, the outer modulation ring 4 is made from titanium. Titanium historically has been considered biocompatible (Lemons et al., (1976), J Biomed Mater Res, 10(4):549-53) in that it does not allow the formation of biofilms on its surface and is principally not culpable in the induction of an immune response. In the third embodiment FIGS. 5A-5D, the outer casing 8 is also made from titanium.

The inner disc 7 of the cranial prosthesis may be manufactured from FDA compliant material capable of being used with ultra-sound imaging with extracted microbubble, i.e. low/no porosity. In particular, the inner disc 7 may be comprised of a biologically-compatible polymeric material approved by the FDA for implantation into the human body, such as polyethylene, polystyrene, acrylic, polymethylpentene (TPX), polymethyl methacrylate (PMMA), a material used in a wide variety of medical applications owing to its low impedance, similar to that of organic fabrics, or any combination thereof. In addition, the inner disc may be comprised of ultrasound compatible ceramics. It should be appreciated that both the inner radio-lucent disc 7 and the outer modulation ring 4 may be made from the same material.

The implementation and application of the cranial prosthesis during a surgical operation occurs in the following manner:

During the course of an intracranial procedure a craniotomy or craniectomy is performed to gain access to the intracranial cavity to perform a procedure. The bone flap size and location are determined by the surgeon based on the patient's pathology.

The surgical planning of the craniotomy may be performed with neuro-navigation in certain instances. On the basis of such planning, the region and shape of the craniotomy are decided, and the desired cranial prosthesis is selected.

The surgeon would use a template to determine the size of the prosthesis. The surgeon could choose a pre-fabricated prosthesis that would come in a small, medium, or large diameter size, for instance, 3-4 cm in diameter, 5-6 cm in diameter or 7-8 cm in diameter, preferably with a thickness between 5-14 mm. This pre-fabricated prosthesis could be used in lieu of the bone flap or incorporated into the bone flap after removal. Alternatively, the prosthesis can be custom-made. In this circumstance the pre-operative images are transferred to a 3D CAD package with "mirroring" of the native bone. In this way as 3D model is built on the basis of which the cranial prosthesis will be produced.

In the event of a customized cranial prosthesis, the device is made of an ultrasound compatible inner core made of polyethylene or other material and an outer titanium rim on the basis of the 3D model, and this is sterilized.

After completion of the procedure, the appropriate size instant cranial prosthesis is positioned and is fixed by means of using suture thread, braces, screws, plates, bone anchors, sutures, wires or other FDA-approved hardware that can pass into the bone of the patient's skull. The prosthesis can be placed in lieu of the bone flap or incorporated within a larger bone flap depending on surgeon preference and patient pathology.

Ultrasound technology is capable of passing through the instant cranial prosthesis making it possible to visualize the intracranial contents post-operatively.

The creation of the ultrasound-compatible cranial prosthesis in substitution of the bone cranial prosthesis of the patient who has been operated on directly enables the attending medical practitioner to perform ultrasound check-ups of the intracranial cavity by the bedside without the need for frequent MRI or CT scanning. Moreover, the modularity of the device allows to monitor the progress of intracranial disease processes and also to administer loco-regional therapies directly into the brain or ventricle thereby bypassing the blood brain barrier. The device also facilitates the use of therapeutic ultrasound with adapters for blood brain barrier disruption, blood clot liquefication, high intensity focused ultrasound (HIFU) or other hither unforeseen applications.

In particular, the use of the cranial prosthesis according to the present invention enables the use of the ultrasound technique combined with the Contrast Enhanced UltraSound (CEUS) method, recently introduced, which makes it possible to identify intracranial lesions with ultrasound contrast means which consist of micro-bubbles of air or inert gases encapsulated in a proteic layer or a layer of polymers. The micro-bubbles typically have an average diameter similar to that of red corpuscles and can be carried in blood capillaries and through the lungs. They inherently produce a strong ultrasound signal owing to the ample acoustic impedance generated by the gas/blood interface, and this signal is further boosted because the micro-bubbles themselves, struck by the ultrasound, echo at specific frequencies, as a function of their diameter, producing an ultrasound signal, as well as reflecting it. Such methodology, which is simple in technical and organizational terms, makes it possible to more effectively evaluate the characteristics of the brain, and distinguish normal brain from pathological states.

The device of the instant application is useful to monitor a number of ailments or conditions. The device will allow for the real-time imaging of brain tumors, such as malignant gliomas or metastatic brain tumors. Currently, brain tumors are visualized by magnetic resonance imaging (MRI), X-ray computed tomography (X-ray CT) or computerized axial tomography scans (CT scan) which takes a "snap shot" of the patient's brain. Real-time observation of the brain is only possible during surgery. The instant device is capable of visualizing the recovering brain outside the operating room at the patient's bedside to monitor brain tumor therapeutics with the instant device's ultrasound imaging capability. In addition to brain tumors, the claimed device is capable of monitoring all aspects of traumatic injuries including, but not limited to, intraparenchymal, subdural, intraventricular, or epidural hematomas. Post aneurysmal subarachnoid hemorrhage with resultant vasospasm can be more accurately monitored when using the Transcranial Doppler System (TCD) (Rimed USA, Inc., New York, N.Y.) in combination with the ultrasound capability of the claimed device. This combination of diagnostic tools provides a life-saving, real-time monitoring of a patient with cerebral vasospasm. The invention can also be used to image and monitor congenital or acquired hydrocephalus at the bedside, in particular, allowing the treating physician the capability of evaluating cerebral spinal fluid diversion (CSF diversion), in a number of situations including, but not limited to, post-traumatic brain injury with extra ventricular drainage; after placement of a ventriculo-peritoneal shunt; and after aneurysmal subarachnoid hemorrhage. Real-time post-operative evaluation of intracranial contents after functional neurosurgery, status post stereo-static biopsy, radio surgery, vascular malformations, congenital anomalies and other similar pathologies can also be performed.

The inventive nature of the claimed cranial prosthesis is its ability to incorporate and engage a number of therapeutic and diagnostic instruments, i.e. "modules" while still maintaining the ability to simultaneously monitor the patient's brain with an ultrasound instrument. In particular, existing intracranial monitoring devices, or specifically developed for use with the prosthesis, may be employed.

Raised intracranial pressure (ICP) can arise as a consequence of traumatic brain injury (TBI), intracranial mass lesions, disorders of cerebrospinal fluid (CSF) circulation, and more diffuse intracranial pathological processes (Dunn L T, (2002), J Neurol Neurosurg Psychiatr, 73(Suppl I):i23-i27). An intracranial pressure (ICP) monitor that directly measures intracranial pressure in the parenchyma, ventricle or the subarachnoid space when clinically important may be modulated into the claimed cranial prosthesis. The claimed cranial prosthesis may include an encapsulated subarachnoid bolt (also referred to as a Richmond bolt or screw), a hollow screw which is inserted through a hole drilled in the skull, used to monitor intracranial pressure. It is placed through the membrane that protects the brain and spinal cord (dura mater) and can record from inside the subdural space. Alternatively, the claimed device is made compatible with the Integra® Camino® Intracranial Pressure Monitoring Kit (Integra LifeSceinces Corp., Plainsboro, N.J.) which monitors intracranial pressure and brain tissue oxygen partial pressure (pbtO2) through a single channel. It fits down the lumen of a catheter which, in turn, may be inserted into one of the pre-formed apertures of the cranial prosthesis or be embedded into the prosthesis at the time of manufacture. The cranial prosthesis of the instant application may also be manufactured to engage a microsensor ICP (DePuy Synthes Co., Raynham, Mass.). For instance, the Codman Microsensor ICP® transducer consists of a miniature pressure strain gauge mounted in a titanium case at the tip of a 100 cm flexible nylon tube of a small size and flexibility allows for low-profile tunneling and kinking of the nylon catheter without breakage or monitoring disturbance. The Codman® Microsensor® transducer monitors intracranial pressure directly at the source—subdural, parenchymal or intraventricular relaying information electronically rather than through a hydrostatic column or fiber optics. The cranial prosthesis of the instant application may be fabricated to include a means in which to engage the nylon tube and deliver it directly to the area of the brain to be monitored. The subject cranial prosthesis may also be designed to include a parenchymal probe, such as the 3PN® by Spielberg (Spielberg GmbH & Co. Kg, Hamburg, Del.). The Probe 3PN® measures intraparenchymal pressure when placed in the parenchyma through a burr hole. The Probe 3PN®, which is traditionally affixed to the patient's skin with a suturing flap, can include a trocar as well, allowing it to be tunneled away from the burr hole. The Probe 3PN® may be already attached to the claimed cranial prosthesis at the time of manufacturing, or the prosthesis may be formulated with a pre-existing bore capable of engaging the Probe 3PN®. In either embodiment, having the capability of using the Probe 3PN® concurrent with the claimed invention upon implantation, reduces the need to conduct subsequent surgeries on the patient to install a parenchymal probe, such as the Probe 3PN®.

If any of the ICP monitors mentioned above detects undesired intracranial pressure in the brain, a ventricular EVD catheter may be also inserted into one of the free access ports found in the outer modulation ring. An external ventricular drainage catheter acts as a pathway to drain cerebral spinal fluid from the patient's ventricles to relieve intracranial pressure. EVD catheters are connected to an external drainage and monitoring system. EVD catheters can be fabricated of radiopaque (barium impregnated) silicone tubing, translucent silicone tubing, or a combination of translucent silicone tubing with a barium strip. In particular, the VentriClear™ II External Ventricular Drainage (EVD) Catheter Set (Medtronic, Minneapolis, Minn.), which allows for external access and drainage of cerebrospinal fluid (CSF) from the ventricles of the brain, is the preferred device for this embodiment. The unique feature of the instant invention allows for the retention of ICP monitor in the brain whilst the ventricular EVD catheter is employed. The ultrasound compatible inner disc further provides the practitioner with the ability to image the brain during drainage of the cerebrospinal fluid combined with the ability to monitor intracranial pressure with the ICP monitor.

The cranial prosthesis of the instant application may also be modulated with a temperature probe. Human brain homeothermy involves interplay between neural metabolic heat production, cerebral blood flow and the temperature of incoming arterial blood. Fluctuation in the temperature of the brain during recuperation may be due to a regulated readjustment in the hypothalamic 'set-point' in response to inflammation and infection, or it may occur as a consequence of damage to the hypothalamus and/or its pathways. Diagnosis of the mechanism of raised temperature; fever v. neurogenic hyperthermia (regulated v. unregulated temperature rise) is difficult to make clinically. Whatever the cause, a 1-2° C. rise in brain or body temperature, especially when it develops early after injury, is widely regarded as harmful (Childs C, (2008), Br J Neurosurg, 22(4):486-96). The cranial prosthesis can be fabricated, as such, to include a temperature probe. For illustrative purpose only, an Integra® Licox® Single Lumen Bolt Brain Tissue Oxygen and Temperature Bolt Kit® (Integra LifeSceinces Corp., Plainsboro, N.J.) may be incorporated into the claimed prosthesis. The Integra Licox Brain Oxygen Monitoring System® measures intracranial oxygen and temperature and is intended as an adjunct monitor of trends of these parameters, indicating the perfusion status of cerebral tissue local to sensor placement. This system utilizes a bore in the cranium to introduce the probe to the part of the brain to be monitored. The instant invention may be pre-fabricated with a bore capable of accepting the Licox® Kit or the kit may be fabricated into the prosthesis at the time of manufacture. In either embodiment, the ability to introduce a temperature probe at the time of implanting the prosthesis into the patient eliminates the need, as mentioned previously, for subsequent invasive procedures, thus minimizing the risks, such as ancillary infection or unintentional physical damage, to the patient's brain.

Another device that may be modulated with the claimed cranial prosthesis is an intracranial blood flow monitor. Lack of blood flow to the brain results in brain ischemia which in turn leads to alterations in brain metabolism, a reduction in metabolic rates, and the creation of an energy crisis (Vespa P et al., (2005), J Cerebral Blood Flow Metab, 25(6):263-74), resulting in brain damage. The cranial prosthesis, for example, may include a QFlow 500™ Perfusion Probe (Hemedex, Inc., Cambridge, Mass.) that continuously quantifies tissue perfusion in absolute physiological units of ml/100 g-min in real time using a thermal diffusion (TD) technique. In neurological applications, the probe permits the calculation of the absolute levels of cerebral blood flow (CBF). The probe is a flexible, radio-opaque catheter that is inserted into the target tissue where it measures perfusion which has been FDA cleared to remain in situ for 10 days. The claimed cranial prosthesis may be pre-fabricated with a bore capable of engaging the catheter of the Perfusion Probe or a catheter may be embedded into the prosthesis at the time of manufacture. Once modulated to the prosthesis, the probe connects to an umbilical cord which in turn connects to the monitor. Another possible intracranial blood flow monitor capable of being modulated to the cerebral prosthesis, is the c-FLOW™ monitor (Ornim, Inc., Foxborough, Mass.) which measures relative changes in blood flow and monitors regional microcirculatory blood flow in tissues, by using sensors. Information reflecting real-time changes in the blood flow, suggesting changes in tissue perfusion, is displayed numerically and graphically on the bedside monitor's screen. The claimed cranial prosthesis may be fabricated with the c-FLOW™ sensors embedded into the device.

The novel cranial prosthesis may include reservoir devices providing cranial access ports with access to the brain. The Integra® reservoir is designed as a closed ventricular access system, facilitating the withdrawal of CSF as well as the delivery of radioisotopes and chemotherapeutic agents. The Integra® CSF Reservoir provides access to the lateral cerebral ventricles via a hypodermic puncture. It is useful in obtaining CSF samples for cytological and chemical studies, for monitoring ventricular fluid pressure and for facilitating ventricular drainage. The reservoir provides easy access to the lateral ventricles and to cystic tumors for the injection of chemotherapeutic agents and/or radio-isotopes. The Convertible CSF Reservoir may be utilized in hydrocephalic patients. Several models are offered, providing the flexibility to accommodate many different treatment protocols. The claimed prosthesis may be prefabricated with a bore or embedded tube which is capable of accepting and directing the catheter to the patient's brain. Integra® Reservoirs are available in various configurations, including: standard, side-inlet, convertible (both burr-hole and flat-bottom) and mini, as well as various sizes.

The claimed cranial prosthesis is also compatible with a Cleveland Multiport Catheter™ (Infuseon Therapeutics, Columbus, Ohio). The Cleveland Multiport Catheter™ uses convection enhanced drug delivery to administer therapeutics directly into brain tissue with higher-volume drug distribution to glioma tumors and tumor-infiltrated brain tissue. Intraparenchymal convection-enhanced delivery (CED) of therapeutics directly into the brain has long been endorsed as a medium through which meaningful concentrations of drug can be administered to patients, bypassing the blood brain barrier. There are a number of indications that would benefit from longer term repeated, intermittent administration of therapeutics (Parkinson's, Alzheimer's, Amyotrophic lateral sclerosis, Brain tumors such as Glioblastoma Multiforme (GBM) and Diffuse intrinsic Pontine Glioma (DIPG), etc.).

The cranial prosthesis may also be equipped with a similar enhanced delivery vehicles, in particular, a reverse, subcutaneous needle access port (Versago Vascular Access, Inc., West Bridgewater, Mass.) as described in U.S. Pat. No. 9,764,124 (Tallarida et al.) and U.S. Pat. No. 9,480,831 (Tallarida et al.), the contents of which, are incorporated herein by reference. The Versago Vascular Access™ port system replaces the typical port septum with a large bore conduit topped with removable dilating needle tips that are externally triggered from the implanted port body. The needle pierces the scalp overlying the device from the inside-out after which the clinician can deliver drugs, cellular therapy, nanospheres or other therapies directly into the cranial chamber. Fluid extraction can also be achieved using the Versago device. This device can be fully incorporated into instant prosthesis. When finished, the clinician replaces the needle tip and pushes the needle back into its housing where it remains until it is redeployed.

An Ommaya reservoir (Medtronic, Minneapolis, Minn.), as described in U.S. Pat. No. 5,385,582 (Ommaya) and U.S. Pat. No. 5,222,982 (Ommaya), the contents of which, are incorporated herein by reference, may also be modulated to the cranial prosthesis. The Ommaya reservoir allows for the introduction or extraction of fluids from the brain. It consists of a small, plastic dome-like container with a small tube or catheter extended outward from the dome. When incorporated into the cranial prosthesis, the dome reservoir is positioned above the prosthesis and the catheter is directed into one of the access ports and into a ventricle of the brain of the patient. Once installed, the Ommaya reservoir can be used to extract cerebral spinal fluid (CSF), to test such fluid or tumor/brain tissue or to introduce chemotherapy directly to the site of the tumor, for example, or into the ventricles for intrathecal chemotherapy. The outer modulation ring can be rotated so as to optimally position the reservoir and its associated catheter to sample CSF or to inject a drug into different areas of the brain. The ultrasound imaging capability of the claimed prosthesis allows the tending surgeon to better locate the region of the brain for treatment avoiding the need to take numerous computerized axial tomography scans (CTs) or magnetic resonance images (MRIs) of the patient to determine if the reservoir was properly placed and/or if treatment is effective.

Another possible port device capable of being modulated to the claimed cranial prosthesis is described in U.S. Pat. No. 5,637,088 (Wenner et al.) which teaches a threaded, dual needle system securely attached to a modified subcutaneous venous access port having an internal reservoir, used for intravenous drug therapy particularly in human cancer treatment. A hollow outer needle is paired with a removable, male-threaded solid inner point and inserted through the patient's tissue and through the port's protective, self-sealing silicon septum, and the solid inner needle is then removed, while the outer needle is left in place. A hollow inner needle is threaded through the outer needle to a depth sufficient to interlock with a female-threaded port receptacle at the base of the port's fluid reservoir and rotated to install. Optional additional threading can permit securing the outer needle to the two inner needles. A breakaway system prevents displacement from unintended pulling of the flow-line. The system thus provides additional protection against needle displacement from venous access ports, the resulting leakage, and the problems caused thereby. This device could be incorporated into the instant prosthesis or placed using an adapter.

Yet another application that may be incorporated into the subject prosthesis is a high intensity focused ultrasound and magnetic imaging device. An example of such a device is the MRgFUS technology (Insightec Ltd., Tirat Carmel, Ill.). Ultrasound is sound waves with frequencies which are higher than those audible to humans. The frequencies used for diagnostic medical imaging are generally in the range of 1 to 18 MHz. Ultrasound may be used therapeutically. High intensity focused ultrasound (HIFU) energy generates heat at a focal point of up to 85° C. to ablate targeted tissue. The frequencies used for therapeutic ultrasound are in the range of 220-680 MHz. Magnetic Resonance Imaging (MRI) is a medical imaging technique that uses magnetic fields and radio waves to form images of the body. The technique is widely used in hospitals for medical diagnosis, staging of disease and follow-up with no exposure to ionizing radiation. An MRI advantage is that it can also provide a temperature measurement (Thermometry) of a scanned organ. MRgFUS uses focused ultrasound to ablate the target tissue under the image and temperature guidance of the MRI. This enables the physician to perform a safe and effective non-invasive treatment with little to no harm to the surrounding tissue and with minimal side effects. MRgFUS uses a multi-element phased array transducer that adjusts to a focal point electronically. The treating physician defines the region of treatment and the system creates a treatment plan accordingly. During treatment, up to 1000 rays of ultrasound are emitted to a focal point. While transforming energy to heat, the ultrasound rays ablate targeted tissue. Guided by an MRI, a clear vision of the treated tissue is acquired. Furthermore, thermal data is analyzed to determine the cumulative thermal impact on the tissue. If necessary, parameters are adjusted to ensure a safe and effective response. The number of ultrasound rays would be greatly reduced by implantation of the instant prosthesis. Moreover, the area to be lesioned using HIFU could simultaneously be monitored and imaged, greatly reducing target planning, ultrasound beam accuracy, and HIFU safety. This would lead to better patient outcomes and dramatically reduce cost and treatment times.

The claimed device is also compatible with a SEPS™ Subdural Evacuating Port System (Medtronic, Minneapolis, Minn.), which may be used to remove a chronic or subacute subdural hematomas and hygromas. The subdural hematoma as it is slowly drained by the SEPS device could also be monitored and imaged.

The term "and/or" as used herein is defined as the possibility of having one or the other or both. For example, "A and/or B" provides for the scenarios of having just A or just B or a combination of A and B. If the claim reads A and/or B and/or C, the composition may include A alone, B alone, C alone, A and B but not C, B and C but not A, A and C but not B or all three A, B and C as components.

The invention, thus conceived, is susceptible of numerous modifications and variations, all of which are within the scope of the appended claims. Moreover, all the details may be substituted by other, technically equivalent elements.

In practice the materials employed, provided they are compatible with the specific use, and the contingent dimensions and shapes, may be any according to requirements and to the state of the art.

Where technical features mentioned in any claim are followed by reference signs, such reference signs have been inserted for the sole purpose of increasing the intelligibility of the claims and accordingly such reference signs do not have any limiting effect on the interpretation of each element identified by way of example by such reference signs.

We claim:
1. A cranial prosthesis comprising:
an ultrasound compatible interior, circular and substantially planar disc;
an outer, circular and substantially planar ring comprising an anterior surface and a posterior surface and having means in which to engage one or more diagnostic instruments and/or one or more intracranial drug delivery systems and/or one or more therapeutic ultrasound devices, wherein said outer, circular and substantially planar ring comprises a bone-contacting surface;
at least one or more diagnostic instruments, one or more intracranial drug delivery systems, and/or one or more therapeutic ultrasound devices detachably affixed to said outer, circular and substantially planar ring; and
a plurality of holes formed in said outer, circular and substantially planar ring, said plurality of holes sized and configured to secure the cranial prosthesis to a patient's existing bone flap using fastening means;
wherein said outer, circular and substantially planar ring may be rotated;
wherein said interior, circular and substantially planar disc allows for the use of an ultra-sound diagnostic device on the patient in which said prosthesis is implanted before, during and after the outer, circular and substantially planar ring engages the one or more diagnostic instruments and/or the one or more intracranial drug delivery systems and/or the one or more therapeutic ultrasound devices;
wherein said cranial prosthesis is biocompatible and sterilizable;
wherein an outer perimeter of said interior, circular and substantially planar disc is directly attached to an inner perimeter of said outer, circular and substantially planar ring;
wherein said means in which to engage one or more diagnostic instruments and/or one or more intracranial drug delivery systems and/or one or more therapeutic ultrasound devices extends through a thickness of said outer, circular and substantially planar ring from the anterior surface to the posterior surface, and is selected from the group consisting of access ports, burr holes, pre-fabricated orifices, embedded tubes, adaptors and plug sockets;
wherein said interior, circular and substantially planar disc is devoid of any means in which to engage one or more diagnostic instruments and/or one or more intracranial drug delivery systems and/or one or more therapeutic ultrasound devices;
wherein the ultrasound compatible interior, circular and substantially flat disc is manufactured from a radiolucent, biologically-compatible, polymeric material selected from the group consisting of polyethylene, polystyrene, acrylic, polymethylpentene and polymethyl methacrylate or from a radio-lucent, biologically-compatible ceramic material.

2. The cranial prosthesis according to claim 1, wherein a medical professional treating the patient into which the cranial prosthesis is implanted is capable of using said one or more diagnostic instruments and/or said one or more intracranial drug delivery systems and/or said one or more therapeutic ultrasound devices while simultaneously employing the interior, circular and substantially planar disc of said prosthesis to use an ultra-sound diagnostic instrument on the patient.

3. The cranial prosthesis according to claim 1,
wherein said one or more diagnostic instruments is selected from the group consisting of a transcranial Doppler system, intra-cranial pressure monitor, microsensor ICP transducer, ventricular drainage monitor, parenchymal probe, temperature probe, intracranial blood flow monitor and a high intensity focused ultrasound and magnetic imaging device;
wherein said one or more intracranial drug delivery systems is selected from the group consisting of a reservoir device with port access, multiport catheters, vascular access port systems, a Cleveland Multiport Catheter, a Versago Vascular Access port system and an Ommaya reservoir; and wherein said one or more therapeutic ultrasound devices is selected from the group consisting of a high intensity focused ultrasound and magnetic imaging device, a high intensity focused ultrasound emitting device used for blood brain barrier disruption and/or blood clot liquification and a device that incorporates MRgFUS technology.

4. The cranial prosthesis according to claim 1, wherein said fastening means is selected from the group consisting of suture thread, braces, screws, plates, bone anchors, sutures and wires.

5. The cranial prosthesis according to claim 1, wherein said cranial prosthesis allows for the use of a nuclear magnetic resonance diagnostic device on the patient in which said prosthesis is implanted while the cranial prosthesis is implanted on the patient.

6. The cranial prosthesis according to claim 3, wherein said cranial prosthesis is capable of:

diagnosing and treating intracranial pathologies selected from the group consisting of tumors, glioblastomas, traumatic brain injuries, intraparenchymal hematomas, intracerebral hematomas, subdural hematomas, epidural hematomas, subarachnoid hemorrhaging with post arrhythmia vasospasms, congenital or acquired hydrocephalus, brain trauma with ventricular drainage, inflammation of the brain, infection of the brain, abscesses, cysts, congenital abnormalities, damage to the hypothalamus and damage to the brain caused by the implanting of a shunt;

monitoring real-time conditions of the brain of a patient onto which the cranial prosthesis is implanted selected from the group consisting of intracranial pressure in the subarachnoid space, brain tissue oxygen partial pressure, subdural pressure, parenchymal pressure, intraventricular pressure, intraparenchymal pressure, temperature, blood flow to and from the brain, tissue perfusions and ventricular fluid pressure; and/or enabling entry into the brain of a patient onto which the cranial prosthesis is implanted to perform various procedures selected from the group consisting of retrieving tissue samples for cytological and chemical analysis, draining ventricular fluid, injecting chemotherapeutic agents or radio-isotopes directly into the brain and performing cellular therapy.

\* \* \* \* \*